United States Patent [19]
Chao

[11] 4,080,260
[45] Mar. 21, 1978

[54] METHOD FOR IMPROVING THE EFFICIENCY OF PROTEIN EXTRACTION FROM YEAST CELLS

[75] Inventor: Kwei C. Chao, Naperville, Ill.

[73] Assignee: Standard Oil Company (Indiana), Chicago, Ill.

[21] Appl. No.: 715,417

[22] Filed: Aug. 18, 1976

[51] Int. Cl.² ............................................. C12D 1/00
[52] U.S. Cl. ........................................ 195/49; 195/82; 195/115; 260/112 R; 426/60; 426/431; 426/656
[58] Field of Search .................. 195/2.5, 28 R, 49, 82, 195/109, 115; 426/60, 431, 656; 260/112 R, 123.5

[56] References Cited

U.S. PATENT DOCUMENTS

| | | | |
|---|---|---|---|
| 3,809,776 | 5/1974 | Chao | 426/60 |
| 3,862,112 | 1/1975 | Ishida et al. | 426/431 |
| 3,867,555 | 2/1975 | Newell et al. | 426/60 |
| 4,007,088 | 2/1977 | Fenci et al. | 426/62 |

*Primary Examiner*—R. B. Penland
*Attorney, Agent, or Firm*—Gregory E. Croft; Arthur G. Gilkes; William T. McClain

[57] ABSTRACT

Isolating protein from yeast cells by alkaline extraction is enhanced by growing a continuous culture of yeasts at the lowest possible dilution rate (space velocity) where the cell yield is not significantly affected and/or by aging the continuous yeast culture in a second stage of continuous fermentation having a residence time from 2 to 4 hours and a pH of from 4 to 10.

18 Claims, No Drawings

METHOD FOR IMPROVING THE EFFICIENCY OF PROTEIN EXTRACTION FROM YEAST CELLS

BACKGROUND OF THE INVENTION

1. Field of the Invention

This invention relates to processes for removing protein from yeast cells by alkaline extraction.

2. Description of the Prior Art

In the food industry, the most important protein ingredients are egg white, casein, sodium caseinate, dried milk solids, and nonfat dry milk. Their functional properties, such as solubility, whippability, emulsification capacity, gellation, etc., are the primary factors determining their utility in food applications. Unfortunately they are expensive and in short supply, and although soy protein isolate and concentrate have been used as replacements, they have a bitter beany taste which restricts their usage level.

These important protein ingredients can potentially be replaced by yeast materials, especially those processed products having a bland flavor and a reduced nucleic acid content. It is necessary to extract the protein within the cells and efficiently recover the protein isolate. Many processes have been developed for this purpose, including the alkali extraction process, which has been well established in the soy industry and is also widely applied to protein extraction from microbial cells.

The efficiency of the alkali extraction process is generally determined by the combined effect of alkalinity, temperature, and the length of reaction time. However, one is not only interested in the efficiency of the protein recovery, but also in the functional quality of the protein product for use as a protein ingredient, i.e. solubility, whippability, etc. Because biological materials such as yeast cells are complex, variations in the nature of the cells occur depending on their cultural history. A yeast culture grown under a specific set of conditions still contains a heterogeneous population consisting of individual cells which may be grouped into various categories based on age, morphology, composition, etc., and those yeast cultures grown under different sets of conditions will contain heterogenous populations which vary even more from each other as a group. It is believed that such different cells or different populations will react differently to alkaline extraction depending upon the changes in cultural conditions.

Accordingly, it is an object of this invention to improve the efficiency of alkaline protein extractions from yeast cells by changing the cultural conditions under which the physiological state of the cells are conditioned specifically for this purpose. This and other objects will become clear upon further reading of this specification.

SUMMARY OF THE INVENTION

In one aspect, the invention resides in an improved process for extracting protein from food yeast cells having the steps of continuously growing a food yeast culture, destroying the permeability barrier of the cells, slurrying the treated yeast cells with an alkaline solution to extract the protein, neutralizing the alkaline slurry, and separating the protein extract from the undigested residue, the improvement comprising growing the continuous culture of yeast cells at a dilution rate of from 0.1 to 0.2 hour$^{-1}$, preferably from 0.12 to 0.15 hour$^{-1}$, to enhance the efficiency of protein extraction.

More specifically, the invention resides in a process for extracting protein from *Candida utilis* yeast cells comprising: continuously growing *Candida utilis* yeast cells on ethanol under oxygen-limiting growth conditions at a dilution rate of from 0.1 to 0.2 hour$^{-1}$; concentrating the yeast cells into a cream; pretreating the cell cream by physical means, such as freezing and thawing, to destroy the permeability barrier of the yeast cells; slurrying the cell material in an alkaline solution to extract the protein; neutralizing the alkaline slurry; separating the extract from the undigested cell material; and dialyzing the extract to remove substances of low molecular weight to produce a crude protein isolate.

In a further aspect, the invention resides in an improved process for extracting protein from food yeast cells having the steps of continuously growing a yeast culture, destroying the permeability barrier of the yeast cells, slurrying the treated yeast cells with an alkaline solution to extract the protein, neutralizing the alkaline slurry, and separating the protein extract from the undigested residue, the improvement comprising aging the continuous yeast culture under starvation conditions in a second stage of continuous fermentation at a pH of from 4 to 10, preferably from 8 to 10. A residence time from 2 to 4 hours is advantageous.

More specifically, the invention resides in a process for extracting protein from *Candida utilis* yeast cells comprising: continuously growing *Candida utilis* yeast cells on ethanol under oxygen-limiting growth conditions; aging the yeast cells in a second stage of continuous fermentation under ethanol-limiting growth conditions at a pH of about 9 and a residence time of about 3 hours; concentrating the yeast cells into a cream; pretreating the cell cream by physical means to destroy the permeability barrier of the yeast cells; slurrying the cell material in an alkaline solution to extract the protein; neutralizing the alkaline slurry; separating the extract from the undigested cell material; and dialyzing the extract to remove substances of low molecular weight to produce a crude protein isolate.

In still further aspect, the invention resides in an improved process for extracting protein from yeast cells having the steps of continuously growing a yeast culture, destroying the permeability barrier of the yeast cells, slurrying the treated yeast cells with an alkaline solution to extract the protein, neutralizing the alkaline slurry, and separating the protein extract from the undigested cell residue, the improvement comprising: growing the continuous culture of yeast cells at a dilution rate of 0.1 to 0.2 hour$^{-1}$, preferably from 0.12 to 0.15 hour$^{-1}$, and aging the continuous yeast culture under starvation conditions in a second stage of continuous fermentation at a pH of from 4 to 10, preferably from 8 to 10. A residence time from 2 to 4 hours is advantageous.

More specifically, the invention resides in a process for extracting protein from *Candida utilis* yeast cells comprising: continuously growing the yeast cells on ethanol under oxygen-limiting growth conditions at a dilution rate of 0.1 to 0.2 hour$^{-1}$, aging the yeast culture in a second stage of continuous fermentation under ethanol-limiting growth conditions at a pH from 8 to 9 and a residence time of from 2 to 4 hours; concentrating the yeast cells into a cream; pretreating the cell cream by physical means to destroy the permeability barrier of the yeast cells; slurrying the cell material in an alkaline solution to extract the protein; neutralizing the alkaline slurry; separating the extract from the undigested cell material; and dialyzing the extract to remove substances of low molecular weight to produce a crude protein isolate.

All food yeasts are within the scope of all aspects of this invention. Most particularly, however, are those yeast cells selected from the group consisting of *Candida utilis, Saccharomyces cerevisiae, Saccharomyces fragilis,* and *Saccharomyces carlsbergensis.*

DESCRIPTION OF SPECIFIC EMBODIMENTS

EXAMPLE 1:

A yeast culture, *Candida utilis* ATCC-9256, was grown on ethanol under oxygen-limiting conditions. The culture was continuously grown at a typical dilution rate (or space velocity) of 0.3 hour$^{-1}$ and the product cell cream was sampled.

The fresh cell cream sample was first subjected to a physical pretreatment of freezing and thawing to destroy the permeability barrier of the yeast cell membrane. The thawed material was suspended in an aqueous slurry and incubated at 45° C. for 10 minutes. This step removes soluble materials, but is not necessary unless the resulting extract is desired for some other application. The cell material was separated from the aqueous permeate and reslurried with a 1 N NaOH solution to give an alkaline slurry having a cell material concentration of 10 weight percent. The slurry was incubated at 45° C. with constant agitation. Samples were taken at the end of 0.5, 1.0, 1.5, and 4.0 hours of incubation to determine the rate of cell digestion and the rate of protein extraction. Each sample was neutralized to a pH of 7.0 by using 6 N HCl. The undigested material was centrifuged, washed, and dried for dry weight determination. The extract was dialyzed against running cold tap water for 40 hours to remove dialyzable substances of low molecular weight. The yield of the nondialyzable materials was determined as the crude protein isolate. The protein content of the crude isolates prepared from the fresh cell cream sample was about 60% whereas that of raw yeast cells was about 42%.

EXAMPLE 2.

The yeast culture of Example 1 was grown under the same conditions, with the exception that the dilution rate was lowered to 0.1 hour$^{-1}$. The product cell cream was sampled and evaluated in the same manner as described in Example 1.

EXAMPLE 3.

The product cell cream of Example 2, having been grown at a dilution rate of 0.1 hour$^{-1}$, was aged by feeding it into a second stage continuous fermentor wherein the growth was ethanol-limited and the pH was maintained at 9.0 by the addition of 10% NH$_4$OH. The dilution rate of the second stage fermentor was set at about 0.3 hour$^{-1}$. The aged product was harvested and subjected to an evaluation of its digestibility by alkali solution and yield of crude protein fraction by the same procedure as described in Example 1.

The results of the evaluations of the three examples are summarized in Tables I and II.

TABLE I

Rate of Cell Digestion by Alkali
(Numbers represent the amount of undigested cell residue expressed as a weight percent of the cell dry weight)

| TIME, (Hours) | 0.5 | 0.1 | 1.5 | 4.0 |
|---|---|---|---|---|
| Example 1 | 47.4 | 40.7 | 37.0 | 33.0 |
| Example 2 | 32.1 | 25.2 | 21.6 | 14.8 |
| Example 3 | 34.4 | 26.6 | 23.3 | 15.0 |

TABLE II

Rate of Protein Extraction by Alkali
(Numbers represent the amount of crude protein isolate expressed as a weight percent of the cell dry weight)

| TIME, (Hours) | 0.5 | 1.0 | 1.5 | 4.0 |
|---|---|---|---|---|
| Example 1 | 39.4 | 44.2 | 48.5 | 51.8 |
| Example 2 | 42.4 | 47.5 | 49.5 | 56.0 |
| Example 3 | 46.7 | 52.7 | 55.0 | 58.2 |

Table I shows that those cells grown at the lower dilution rate of 0.1 hour$^{-1}$ are more readily digested by the alkali solution than those grown at the higher dilution rate of 0.3 hour$^{-1}$, although the aging process appears to have little effect on the digestion rate.

Table II shows that those cells grown at the lower dilution rate of 0.1 hour$^{-1}$ also give a higher yield of crude protein isolate than those grown at a dilution rate of 0.3 hour$^{-1}$. The aged cells of Example 3 show an even greater improvement in yield of crude protein isolate. The yeast protein isolates obtained from these improvements possess good functionality for food applications.

It will be obvious to those skilled in the art that many variations can be made from the specific embodiments shown for purposes of illustration without departing from the scope of this invention.

I claim:

1. In a process for extracting protein from food yeast cells having the steps of continuously growing a food yeast culture, destroying the permeability barrier of the yeast cells, slurrying the treated yeast cells with an alkaline solution to extract the protein, neutralizing the alkaline slurry, and separating the protein extract from the undigested residue, the improvement comprising growing the continuous culture of yeast cells at a dilution rate of from 0.1 to 0.2 hour$^{-1}$ to enhance the efficiency of protein extraction.

2. The process of claim 1 wherein the dilution rate is from 0.12 to 0.15 hour$^{-1}$.

3. The process of claim 1 wherein the yeast cells are selected from the group consisting of *Candida utilis, Saccharomyces cerevisiae, Saccharomyces fragilis,* and *Saccharomyces carlsbergensis.*

4. A process for extracting protein from *Candida utilis* yeast cells comprising:
   (a) continuously growing *Candida utilis* yeast cells on ethanol under oxygen-limiting growth conditions at a dilution rate of 0.1 to 0.2 hour$^{-1}$;
   (b) concentrating the yeast cells into a cream;
   (c) pretreating the cell cream by physical means to destroy the permeability barrier of the yeast cells;
   (d) slurrying the cell material in an alkaline solution to extract the protein;
   (e) neutralizing the alkaline slurry;
   (f) separating the extract from the undigested cell material; and
   (g) dialyzing the extract to remove substances of low molecular weight to produce a crude protein isolate.

5. The process of claim 4 wherein the dilution rate is from 0.12 to 0.15 hour$^{-1}$.

6. The process of claim 5 wherein the physical means of pretreatment is freezing and thawing.

7. In a process for extracting protein from food yeast cells having the steps of continuously growing a yeast culture on a carbon source substrate, destroying the permeability barrier of the yeast cells, slurrying the treated yeast cells with an alkaline solution to extract the protein, neutralizing the alkaline slurry, and separating the protein extract from the undigested residue, the improvement comprising aging the continuous yeast culture under substrate-limited conditions in a second stage of continuous fermentation at a pH of from 4 to about 10 to increase the protein yield from the extraction.

8. The process of claim 7 wherein the pH is about 9.

9. The process of claim 7 wherein the residence time for the second stage of continuous fermentation is from 2 to 4 hours.

10. The process of claim 7 wherein the yeast cells are selected from the group consisting of *Candida utilis, Saccharomyces cerevisiae, Saccharomyces fragilis,* and *Saccharomyces carlsbergensis.*

11. A process for extracting protein from *Candida utilis* yeast cells comprising:
   (a) continuously growing *Candida utilis* yeast cells on ethanol under oxygen-limiting growth conditions;
   (b) aging the yeast cells in a second stage of continuous fermentation under ethanol-limiting growth conditions at a pH of about 9 and a residence time of about 3 hours;
   (c) concentrating the yeast cells into a cream;
   (d) pretreating the cell cream by physical means to destroy the permeability barrier of the yeast cells;
   (e) slurrying the cell material in the alkaline solution to extract the protein;
   (f) neutralizing the alkaline slurry;
   (g) separating the extract from the undigested cell material; and
   (h) dialyzing the extract to remove substances of low molecular weight to produce a crude protein isolate.

12. In a process for extracting protein from food yeast cells having the steps of continuously growing a yeast culture on a carbon source substrate, destroying the permeability barrier of the yeast cells, slurrying the treated yeast cells with an alkaline solution to extract the protein, neutralizing the alkaline slurry, and separating the protein extract from the undigested cell residue, the improvement comprising:
   (a) growing the continuous culture of yeast cells at a dilution rate of from 0.1 to 0.2 hour$^{-1}$; and
   (b) aging the continuous yeast culture under substrate-limited conditions in a second stage of continuous fermentation at a pH of from 4 to about 10 to increase the protein yield from the extraction.

13. The process of claim 12 wherein the dilution rate is from 0.12 to 0.15 hour$^{-1}$.

14. The process of claim 12 wherein the pH in the second stage of continuous fermentation is from 8 to 10.

15. The process of claim 12 wherein the second stage of continuous fermentation has a residence time of from 2 to 4 hours.

16. The process of claim 12 wherein the yeast cells are selected from the group consisting of *Candida utilis, Saccharomyces cerevisiae, Saccharomyces fragilis,* and *Saccharomyces carlsbergensis.*

17. A process for extracting protein from *Candida utilis* yeast cells comprising:
   (a) continuously growing the yeast cells on ethanol under oxygen-limiting growth conditions at a dilution rate of 0.1 to 0.2 hour$^{-}$.
   (b) aging the yeast culture in a second stage of continuous fermentation under ethanol-limiting growth conditions at a pH of from 8 to 9 and a residence time of from 2 to 4 hours;
   (c) concentrating the yeast cells into a cream;
   (d) pretreating the cell cream by physical means to destroy the permeability barrier of the yeast cells;
   (e) slurrying the cell material in an alkaline solution to extract the protein;
   (f) neutralizing the alkaline slurry;
   (g) separating the extract from the undigested cell material; and
   (h) dialyzing the extract to remove substances of low molecular weight to produce a crude protein isolate.

18. A process for extracting protein from *Candida utilis* yeast cells comprising:
   (a) continuously growing the yeast cells on ethanol under oxygen-limiting growth conditions at a dilution rate of from 0.12 to 0.15 hour$^{-1}$;
   (b) aging the yeast culture in a second stage of continuous fermentation under ethanol-limiting growth conditions at a pH of about 9 and a residence time of from 3 hours;
   (c) concentrating the yeast cells into a cream;
   (d) pretreating the cell cream by freezing and thawing to destroy the permeability barrier of the yeast cells;
   (e) slurrying at about 45° C. the pretreated cell cream with water and incubating the slurry to remove solubles;
   (f) separating the cell material from the aqueous permeate;
   (g) slurrying the cell material in an alkaline solution to extract protein;
   (h) neutralizing the alkaline slurry;
   (i) separating the extract from the undigested cell material; and
   (j) dialyzing the extract to remove substances of low-molecular weight to produce a crude protein isolate.

* * * * *

UNITED STATES PATENT OFFICE
CERTIFICATE OF CORRECTION

Patent No. 4,080,260        Dated March 21, 1978

Inventor(s) Kwei C. Chao

It is certified that error appears in the above-identified patent and that said Letters Patent are hereby corrected as shown below:

Column 6, line 16 "to 0.2 hour$^{-}$" should be -- to 0.2 hour$^{-1}$ --

Column 6, lines 45-47 "slurrying at about 45°C the pretreated cell cream with water and incubating the slurry to remove solubles;" should be -- slurrying the pretreated cell cream with water and incubating the slurry at about 45°C to remove solubles --

Signed and Sealed this

Fifteenth Day of May 1979

[SEAL]

Attest:

RUTH C. MASON  
Attesting Officer

DONALD W. BANNER  
Commissioner of Patents and Trademarks